United States Patent [19]

Roth et al.

[11] Patent Number: 4,701,323

[45] Date of Patent: Oct. 20, 1987

[54] VACCINES FOR COUNTERACTING INHIBITION OF NEUTROPHIL DEGRANULATION

[75] Inventors: James A. Roth; Peter C. Canning; Yu-Wei Chiang, all of Ames, Iowa

[73] Assignee: Iowa State University Research Foundation, Inc., Ames, Iowa

[21] Appl. No.: 790,343

[22] Filed: Oct. 23, 1985

[51] Int. Cl.[4] .................... A61K 39/02; A61K 39/385
[52] U.S. Cl. ........................................ 424/88; 424/92; 424/85; 530/405; 530/406; 530/363
[58] Field of Search ............................ 424/88, 92, 85; 530/405, 406

[56] References Cited

U.S. PATENT DOCUMENTS

| | | | |
|---|---|---|---|
| 3,725,545 | 4/1973 | Maes | 424/88 |
| 4,285,930 | 8/1981 | Likhite | 424/88 X |
| 4,460,575 | 7/1984 | d'Hinterland et al. | 424/88 X |

OTHER PUBLICATIONS

Halloran et al., (1966), J. Immunology, 96:373–378.
Erlanger et al., (1964), Pro. Natl. Acad. Sci. U.S.A., 52:68–74.
Butler et al., (1962), Pro. Natl. Acad. Sci. U.S.A., 48:1597–1602.
Densen and Mandel, "Reviews of Infectious Diseases", vol. 2, No. 5, Sep.–Oct. 1980, pp. 817–838.
Lowrie et al., (1975), Nature, 254:600–602.
Lowrie et al., (1979), J. Gen. Microbiol., 110:431–441.
Riches et al., (1985), J. Leukocyte Biol., 37:545–557.

*Primary Examiner*—Howard E. Schain
*Attorney, Agent, or Firm*—Tilton, Fallon, Lungmus & Chestnut

[57] ABSTRACT

Vaccines for counteracting inhibition of neutrophil degranulation by pathogenic cellular microorganisms comprise one or more purines conjugated to antigenic carriers. The purines include adenine and/or guanine in the form of a base, nucleoside, or nucleotide. The vaccines can be used with cattle to increase resistance to infections by *Brucella abortus* (brucellosis) and/or *Haemophilus somnus* (thromboembolic meningoencephalitis) and related symptomatic complex.

17 Claims, No Drawings

VACCINES FOR COUNTERACTING INHIBITION OF NEUTROPHIL DEGRANULATION

FIELD OF INVENTION, BACKGROUND, AND PRIOR ART

The field of the invention is vaccines for preventing or reducing the severity of infectious diseases. More particularly, the invention is concerned with vaccines against pathogenic microorganisms which resist neutrophil destruction by inhibiting degranulation.

The mechanisms by which bacteria resist phagocytic destruction have been summarized by Densen and Mandel: "Reviews of Infectious Diseases," Vol. 2, No. 5, Sept.-Oct. 1980, pages 817-838. Relevant here is the phagocytosis sequence in which polymorphonuclear neutrophils (PMNs) ingest invading bacteria and the PMNs granules move toward and merge with the phagosome containing the ingested microorganisms, releasing enzymes which assist in the destruction of the bacteria. If degranulation is inhibited or does not occur at all, ingested microorganisms may be able to survive within the PMNs. In Table 1 (page 821), Densen and Mandel list some pathogens which have been reported to inhibit degranulation, including Mycobacteria[1] species *M. tuberculosis, M. microti,* and *M. bovis.* and also *Toxoplasma gondii.* It appears, however, that prior reports have related to fixed macrophages in the tissues rather than circulating PMNs.

Prior to the experimental work leading to the present invention, the mechanisms by which certain microorganisms inhibit degranulation of PMNs is not known to have been elucidated. In macrophages, cyclic AMP (cAMP), a well-known cell regulator, was reported to play a role in the inhibition of macrophage degranulation by Mycobacteria. See Lowrie et al. (1975), *Nature,* 254:600-602; and Lowrie et al. (1979), *J. Gen. Microbiol.,* 110:431-441. These researchers found that macrophages ingesting live mycobacteria had increased concentrations of intracellular cyclic AMP. It was suggested that at least part of the cAMP may have been produced by the bacteria but this speculation was not confirmed. Cyclic AMP as well as cyclic GMP (cGMP) are known to be important intracellular regulatory molecules. In general, increased intracellular cAMP tends to inhibit cell functions while increased cGMP enhances cell functions.

The regulation of macrophage lysosomal secretion by adenosine and related compounds has recently been reported: Riches, et al. (1985), *J. Leukocyte Biol.,* 37:545-557. Riches et al. found that zymosan particle-stimulated beta-galactosidase secretion by mouse peritoneal macrophages could be inhibited by adenosine, AMP, and related compounds, as well as guanosine.

SUMMARY OF INVENTION

Polymorphonuclear neutrophils (PMNs) comprise a major cellular defense mechanism for protecting animals from infection by cellular organisms (bacteria, fungi, etc.). In the experimental work leading to this invention, bacterial infections of cattle which are not killed effectively by neutrophils were studied. One of these pathogens is *Brucella abortus,* which is the causative agent of bovine brucellosis. Another is *Haemophilus somnus,* which causes several disease syndromes in cattle, including thromboembolic meningoencephalitis, and a symptomatic complex of respiratory infection, septicemia, and thrombosis. Both microorganisms were studied.

It was found that *B. abortus* and *H. somnus* both produce factors which inhibit degranulation of PMNs, and that neutrophil ingestion of these bacteria does not result in the usual process of neutrophil phagocytosis. Surprisingly, after extensive laboratory work, the inhibiting factors were identified as purines, both pathogens liberating adenine and GMP. Guanine was also detected for *H. somnus.* Even more surprisingly, it was found that these purines in pure form are capable of inhibiting degranulation of PMNs. The conclusion indicated is that neutrophil degranulation is depressed and may be totally inhibited by certain adenine or guanine containing water-soluble purines.

These discoveries have led to a vaccine for counteracting inhibition of neutrophil degranulation. The vaccine comprises a parenterally-administrable sterile aqueous solution of one or more purines conjugated to antigenic proteins. The protein conjugated to purines may contain adenine or guanine as a base, nucleoside or nucleotide. The conjugated purines are capable of generating antibodies which are specific to each purine type (viz. adenine or guanine types). Antisera to adenosine, for example, is reactive with adenine, adenosine, and AMP. Similarly, antisera to guanosine is reactive with guanine, guanosine, and GP. However, adenosine-induced antisera has little cross-reaction with guanine and related purines. Similarly, guanosine antisera does not appreciably react with adenine compounds.

In a preferred embodiment, the vaccine contains each of the two kinds of purines conjugated to antigenic proteins. For example, the vaccine preferably contains adenosine and guanosine in nucleoside form. The antibodies generated by this combination vaccine are reactive with both types of purines.

Degranulation inhibitors produced by bacteria such as *B. abortus* and *H. somnus* are visualized as concentrated in the cell envelopes, and particularly on their outer surfaces. In a postulated mechanism, the vaccinated animals produce antipurine antibodies which bind to the purines on the outer surfaces of the bacterial cells prior to their ingestion by PMNs. The degranulation inhibitory action of the bacterial purines is thereby neutralized. Ingestion of the bacteria by the PMNs can then result in the usual process of destruction by neutrophil degranulation and related mechanisms.

DETAILED DISCLOSURE

Purines for use in preparing vaccines of this invention are available commercially. One or more of the following purines should be employed:

| Adenine Type | Guanine Type |
| --- | --- |
| adenine | guanine |
| adenosine | guanosine |
| 2'-deoxyadenosine | 2'-deoxyguanosine |
| AMP | GMP |
| dAMP | dGMP |

Adenine and guanine are referred to as bases, while adenosine, 2'-deoxyadenosine, guanosine, and 2'-deoxyguanosine are nucleosides. AMP (adenosine 5'-phosphate), dAMP (deoxyadenosine 5'-phosphate), GMP (guanosine 5'-phosphate) and dGMP (deoxyguanosine 5'-phosphate) are nucleotides. For the purposes of this invention, the purines may be in the form of bases, nucleosides or nucleotides. However, the use of adenosine and guanosine in nucleoside form is believed to produce the most effective antisera and is therefore preferred.

For use in the vaccine, the purines are attached to proteins having antigenic properties. The protein "carriers" for the purines enhance the production of antibodies to the purines. The protein may comprise animal or human serum albumin, keyhole limpet hemocyanin, tetanus toxoid, ovalbumin, etc.

Purines may be conjugated to the carrier proteins using carbodiimide coupling as described by Halloran et al. (1966), *J. Immunology*, 96:373–378. Ribonucleosides and ribonucleotides such as adenosine, guanosine, AMP dAMP, GMP and dGMP may be conjugated to proteins by the periodate reaction procedure of Erlanger et al. (1964), *Pro. Natl. Acad. Sci. U.S.A.*, 52:68–74. See, also, Butler et al. (1962), *Pro. Natl. Acad. Sci. U.S.A.*, 48:1597–1602. As reported by Erlanger and co-workers, purines and pyrimidines conjugated to antigenic proteins are capable of generating purine or pyrimidine specific antibodies.

The conjugated purines are water-soluble, and can therefore be dissolved in water for vaccine use. For example, the aqueous carrier may comprise normal saline. The concentration of the aqueous solution is not critical. For example, the concentrations may range from about 0.25 to 5.0 milligrams of protein conjugate per milliliter of solution. Where more than one protein conjugate is present, such as mixed conjugates of adenosine and guanosine, each of the conjugates may be present in concentrations of from about 0.1 to 2.5 milligrams per milliliter. A typical antibody producing dose for large domestic animals is from about 0.5 to 10.0 milligrams of each type of conjugate per dose. For example, if the vaccine comprises a mixture of protein conjugates of both adenosine and guanosine, as preferred, each of the types of conjugates will be used in the specified dose amounts.

Although not essential, if desired an adjuvant may be included in the vaccine. For example, suitable adjuvants are: (1) Freund's incomplete adjuvant which is emulsified with an equal volume of the aqueous purine containing vaccine and administered in 2 ml doses subcutaneously; or (2) a 0.2% solution of alum which had adsorbed the purine containing vaccine and is administered in 2 ml doses subcutaneously.

The vaccine should be prepared under sterile conditions so that the solutions are sterile, and the solutions should be aseptically packaged. Packaging in vials can involve sterilization either before or after packaging. The vials may contain one or more doses, and may be provided with a closure pierceable by a hypodermic needle. The vaccine for cattle may be packaged as a sterile solution in multidose dark-glass vials containing 10 doses (20 ml), 25 doses (50 ml) or 50 doses (100 ml). The vials may be sealed with a closure pierceable by a hypodermic needle and would be appropriately labeled.

The vaccines of this invention are generally suitable for use in counteracting inhibition of neutrophil degranulation by pathogenic cellular microorganisms. The vaccines are designed for increasing resistance to pathogenic cellular microorganisms which liberate purines as a defense to neutrophils. The vaccines are administered to the animals subject to the infection, and a sufficient amount of the conjugated purines are given to generate antibodies to adenine and/or guanine. Preferably, as described above, the vaccine is formulated and administered to generate antibodies to both adenine and guanine-type purines.

The vaccines of this invention are believed to be particularly effective in improving the resistance of cattle to *B. abortus* and *H. somnus*. It will be apparent, however, that the vaccines of this invention have wider applicability, and can be used to increase the resistance of cattle and other animals to infections by bacteria, fungi and yeasts, which have developed a defense mechanism against neutrophils involving the liberation of adenine and/or guanine-type purines. The vaccines of this invention are particularly advantageous for use with domestic animals, including cattle, swine, sheep, horses, and poultry. However, it is believed that they will also have applications in human preventive medicine. Specific diseases of domestic animals caused by microorganisms which resist destruction by neutrophils and which may be prevented by the vaccines include: Salmonellosis, Listeriosis, Tuberculosis, Histoplasmosis, and Blastomycosis (all of which occur in many domestic species), and *Rhodococcus equi* infection of foals, *Bordetella bronchiseptica* of swine, and Paratuberculosis in cattle.

The vaccines are administered parenterally. The preferred route is subcutaneous (S.C.) but other routes can be used, including intramuscular (I M.) and intravenous (I.V.).

The scientific and practical aspects of the present invention are further illustrated by the following examples.

EXAMPLE I

A vaccine for immunization of cattle against *B. abortus* and/or *H. somnus* can be prepared as follows. The vaccine will contain guanosine and adenosine linked to keyhole limpet hemocyanin (KLH), using the procedure of Erlanger and Beiser. See Butler et al. (1962), *Proc. Natl. Acad. Sci. USA* 48:1597–1602. The guanosine or adenosine (100 mg) is dissolved in 5.0 ml of 0.1 M $NaIO_4$ and allowed to stand 20 minutes at room temperature. Excess $NaIO_4$ is decomposed by the addition of 0.3 ml 1.0 M ethylene glycol followed by a 5-minute period at room temperature. The reaction mixture is then added to an aqueous solution (10 ml) of 280 mg KLH which had been adjusted to pH 9–9.5 with 5% potassium carbonate. Stirring is continued for 45 minutes, the pH being maintained at 9–9.5 with 5% potassium carbonate. A solution of 150 mg of $NaBH_4$ in 10 ml $H_2O$ is then added, followed one hour later by adjustment of the pH to 8.5 using 1 M $NH_4OH$. The solution is then dialyzed, lyophilized, and rehydrated in saline to a concentration of 2.0 mg of protein per ml. The guanosine and adenosine conjugates are then mixed together into one solution.

The alum adjuvanted vaccine is prepared by adding 2.33 ml of 10 percent $AlCl_3$ to 50 ml of the adenosine-guanosine conjugate mixture then adding sufficient 20 percent NaOH to bring the reaction to pH 7.0. The solution is then diluted to 100 ml wi.th saline to produce a vaccine containing 1.0 mg of protein (conjugated to a.denosine and guanosine) per ml adsorbed to alum which serves as the adjuvant. The vaccine is prepared aseptically from sterile ingredients, or it can be sterilized by irradiation and aseptically packaged as a sterile solution in multidose glass vials containing 20 ml, 50 ml, or 100 ml of vaccine. The vials can be sealed with a closure pierceable by a hypodermic needle and would be appropriately labeled. Cattle are immunized with two 2.0 ml doses of vaccine administered subcutaneously 2 weeks apart.

EXAMPLE II

The preparation of guanosine monophosphate (GMP) antigen suitable for production of anti-nucleotide antibodies in rabbits was accomplished using a modification of the procedures of Halloran and Parker (1966), *J. Immunol.* 96:373. All chemicals used in this work were purchased from Sigma Chemical Co., St. Louis Briefly, 10.0 mg of GMP was mixed with 4.0 mg of either human serum albumin (HSA) or keyhole limpet hemocyanin (KLH) in 1.0 ml of tissue culture grade water. The pH of the solution was adjusted to 7.5 and 10 mg of 1-ethyl-3-diisopropylaminocarbodiimide-HCl (EDC) as added to the reaction mixture. The solution was incubated for 24 hrs. at room temperature in the dark. Following incubation, the reaction mixture was dialyzed at 4° C. against 0.01 M Tris chloride, pH 7.6, for 18 hrs. The dialyzed solution was then evaluated by scanning U.V. spectrophotometry to confirm coupling. The solution was then restored to isotonicity with the addition of 10× phosphate buffered saline.

Four rabbits were used for the production of specific antisera. Each rabbit received one of four antigen preparatior:s in two 250 μl (protein dry wt.) doses spaced two weeks apart as follows:
(1) GMP-HSA, IV
(2) GMP-HSA, IM with Freund's incomplete adjuvant
(3) GMP-KLH, IV
(4) GMP-KLH, IM with Freund's incomplete adjuvant.

Following the second and fourth weeks, serum samples were collected and evaluated by an ELISA procedure to detect specific anti-nucleotide antibody.

The ELISA plates were set up such that the sera raised against HSA-coupled GMP were evaluated against KLH-coupled GMP while the sera raised against KLH-coupled GMP were evaluated against HSA-coupled GMP. This system allowed detection of antibody molecules directed against the nucleotide hapten. The rabbit which received GMP-KLH, IV, produced anti-GMP antibody with a maximum titler of 1:512 (OD=0.524).

EXAMPLE III

1. Preparation of Immunogen.

Guanosine-KLH, GMP-KLH, and GMP-BSA were pepared by the method of Erlanger and Beiser (Proc. Natl. Acad. Sci. USA 48:1597, 1962).

2. Immunization of rabbits with GMP-BSA.

A total of 3 rabbits were used. The procedure for immunization with GMP-BSA (without adjuvant) is shown in the following table.

| Day | Treatment |
|---|---|
| 0 | 2 mg GMP-BSA in PBS; S.C. |
| 7 | 2 mg GMP-BSA in PBS; I.V. |
| 14 | 2 mg GMP-BSA in PBS; I.V. |
| 21 | 1st bleeding |
| 27 | 2 mg GMP-BSA in PBS |
| 34 | 2nd bleeding |
| 41 | 2 mg GMP-BSA in PBS; I.V. |
| 48 | 3rd bleeding |
| 62 | 2 mg GMP-BSA in PBS; I.V. |
| 69 | 4th bleeding |

3. Anti-GMP response in rabbits.

The antibody titer was detected by ELISA using GMP-KLH as the antigen. The table below shows the anti-GMP antibody titers of the three rabbits:

|  | Rabbit #1 | Rabbit #2 | Rabbit #3 |
|---|---|---|---|
| 1st bleeding | 1:1280 | 1:320 | 1:640 |
| 2nd bleeding | 1:5120 | 1:320 | 1:640 |
| 3rd bleeding | 1:5120 | 1:320 | 1:640 |
| 4th bleeding | 1:5120 | 1:320 | 1:1280 |

4. Immunization of Calves with GMP-KLH.

| Day | Treatment |
|---|---|
| 0 | 1 mg GMP-KLH or guanosine-KLH in FIA; S.C |
| 7 | 1 mg GMP-KLH or guanosine-KLH in FIA; S.C 1st bleeding |
| 14 | 1 mg GMP-KLH or guanosine-KLH in FIA; S.C 2nd bleeding |

5. Anti-GMP response in calves.

The antibody titer was determined using an enzyme-linked immunosorbent assay (ELISA) with GMP-BSA bound to the ELISA plate as the test antigen.

|  | Calf #1 | Calf #2 |
|---|---|---|
| 1st bleeding | 1:320 | 1:160 |
| 2nd bleeding | 1:20,480 | 1:10,240 |

6. Anti-guanosine response in calves.

The antibody titer was determined using an ELISA with guanosine-BSA bound to the ELISA plate as the antigen.

|  | Calf #3 | Calf #4 |
|---|---|---|
| 1st bleeding | 1:200 | 1:100 |
| 2nd bleeding | 1:6,400 | 1:1,600 |

7. Cross reactivity of the anti-guanosine antibody.

The presence of free guanine, guanosine, d guanosine, GMP and dGMP in the ELISA assay strongly inhibited the binding of antiguanosine antibody to the guanosine-BSA bound to the plate. Thus indicating that antibody directed against guanosine will also bind to each of these other guanine-containing molecules. The presence of free adenine, adenosine, or AMP in the ELISA assay did not inhibit binding of anti-guanosine antibody to guanosine, therefore, indicating that anti-guanosine antibody does not cross-react with these adenine-containing molecules.

8. Cross reactivity of the bovine anti-GMP antibody.

The presence of free GMP, dGMP, and AMP in the ELISA assay strongly inhibited the binding of anti-GMP antibody to GMP, indicating that antibody to GMP will also bind to each of these molecules. The presence of free guanine, guanosine, and d guanosine in the ELISA assay only weakly inhibited the binding of anti-GMP antibody to GMP. The presence of free adenine or adenosine in the ELISA assay did not inhibit the binding of anti-GMP antibody to GMP. These observations indicate that the ribose phosphate portion of GMP is immunodominant and that much of the antibody formed is against this portion of the molecule. This would explain why the anti-GmP serum binds more strongly to AMP than to guanine and guanosine.

9. Abbreviations:
GMP=Guanosine monophosphate
BSA=Bovine serum albumin
KLH=Keyhole limpet hemocyanin
FIA=Freund's incomplete adjuvant
PBS=phosphate buffered saline
S.C.=Subcutaneously
I.V.=Intravenously

EXAMPLE IV

Two components responsible for the inhibition of bovine neutrophil degranulation were extracted from the bacteria by gentle heating. The inhibitory components were isolated by membrane filtration and reverse phase high performance liquid chromatography and designated as fractions 3b and 10. Preliminary characterization and identification of the molecules were accomplished through both physical and chemical analyses. The results of these studies indicated that neither fraction 3b nor 10 contained detectable proteins or lipids. Fraction 3b contained a small amount of carbohydrate while fraction 10 did not contain a detectable amount. Both fractions exhibited maximum absorbence of ultraviolet light at 260n.m and had molecular weights of less than 1,000 daltons. These results are consistent with the properties of nucleotide or nucleotide-like molecules. Fractions 3b and 10 were analyzed by reverse phase high performance liquid chromatography and thin layer chromatography and compared with nucleotide and base standards. These investigations indicated the fraction 3b co-eluted and co-migrated with 5'-guanosine monophosphate while fraction 10 co-eluted and co-migrated with adenine. The biological effects of 5'-guanosine monophosphate, adenine, and $B.$ $abortus$ fractions 3b and 10 on bovine neutrophil functions were determined. None of the compounds affected the ability of neutrophils to ingest bacteria or produce superoxide anion in response to ingestion. Iodination activity of neutrophils (a measure of myeloperoxidase-$H_2O_2$-halide activity) was inhibited to approximately 65% of control by similar concentrations of 5'-guanosine monophosphate and fraction 3b. Iodination was also suppressed to approximately 80% of control by similar concentrations of adenine and fraction 10. These results indicate that $B.$ $abortus$ fractions 3b and 10 are 5'-guanosine monophosphate and adenine, respectively, and it is these materials which are at least in part responsible for the survival of the bacteria within bovine neutrophils.

EXAMPLE V $H.$ $somnus$ fractions which are inhibitory to degranulation by bovine PMNs were isolated by the following procedures: A washed suspension of $H.$ $somnus$ in PBS was either heat-extracted at 60° C: for 1 hour or incubated at 37° C. for 2 hours followed by centrifugation. The supernatant was collected and filtered through an ultrafiltration membrane with a molecular weight (MW) cutoff of 300,000 daltons and then through another membrane with MW cutoff of 1,000 daltons. The final filtrate was termed HEIF-60 for the fraction isolated by heat extraction at 60° C. and HEIF-37 for the fraction isolated by incubation at 37° C.

Preliminary chemical characterization indicated that both fractions contained components that were chemically and physically similar to nucleotides or nucleotide-like compounds. Consequently, the components present in each fraction were separated by using a high performance liquid chromatography system equipped with a C-18 reverse-phase column under the chromatographic conditions which were previously described for separation of nucleotides or nucleotide-like compounds from bacterial cells (S.M. Payne and B.N. Ames, Anal. Biochem. 1982, 123: 151–161).

The components present in each fraction were identified by the following procedures which were described elsewhere (R. A. Harwick et al., 1979, J. Chromatog., 168:659–676).

1. Retention time—Commercially available standards with a similar retention time to an unknown peak were co-injected with the fraction and changes in peak shape noted. Standards which caused an unknown peak to increase in height without the appearance of a shoulder or unusual peak broadening were considered to have the same retention time as the unknown peak. Accordingly, the components present in HEIF-60 were tentatively identified as cytosine, uracil, guanine, guanosine, adenine, CMP, UMP, GMP, AMP, CDP, GDP, and ADP. HEIF-37 contained the same components but in different quantities. The presence of cytosine, uracil, guanine, guanosine, and adenine was further confirmed by using the same technique but under different chromatographic conditions which were described for the identification of nucleosides, bases and other UV-absorbing, low-molecular weight compounds (K. Nakano et al. 1982, J. Chromatog. 233:51–60).

2. Enzymatic treatments—The presence of ribonucleotides and guanine in each fraction was further confirmed by treating each fraction with 5'-nucleotidase and guanase, respectively. Treatment with 5'-nucleotidase converted all ribonucleotides into their corresponding ribonucleosides, whereas treatment with guanase caused the appearance of a peak co-eluting with xanthine.

When all the identified compounds were titrated for their effect on degranulation by bovine PMNs, most of them, except cytosine and CDP, were found to be inhibitory. The inhibition caused by these compounds was dose-dependent. When the concentrations of the components in each fraction were estimated, it was found that guanine and adenine had concentrations high enough to cause most of the suppressive activity observed for HEIF-37, whereas guanine and GMP were the major suppressive components in HEIF-60.

We claim:

1. A vaccine for counteracting inhibition of neutrophil degranulation by pathogenic cellular microorganisms, comprising an aseptically-packaged, parenterally-administrable sterile aqueous solution of at least one purine conjugated to an antigenic protein, each of said conjugated purines containing adenine or guanine as a base, nucleoside, or nucleotide thereof, the amount of said conjugated purine in said packaged vaccine providing single or multiple vaccine doses effective for generating antibodies to adenine and/or guanine.

2. The vaccine of claim 1 in which said conjugated purine at least contains adenine as a base, nucleoside, or nucleotide.

3. The vaccine of claim 1 in which said conjugated purine at least contains adenine in a form selected from adenine, adenosine, 2'-deoxyadenosine, AMP and dAMP.

4. The vaccine of claim 1 in which said conjugated purine at least contains guanine as a base, nucleoside, or nucleotide.

5. The vaccine of claim 1 in which said conjugated purine at least contains guanine in a form selected from guanine, guanosine, 2'-deoxyguanosine, GMP, and dGMP.

6. The vaccine of claim 1 which contains protein conjugated adenosine in admixture with protein conjugated guanosine.

7. A vaccine for counteracting inhibition of neutrophil degranulation by pathogenic microorganisms, comprising an aseptically-packaged, parenterally-administrable sterile aqueous solution of a mixture of at least two kinds of purines conjugated to antigenic protein, one of said kinds of conjugated purine containing adenine and the other kind containing guanine, said purines being present in the form of bases, nucleosides, or nucleotides, the amount of each of said kinds of conjugated purines in said packaged vaccine providing single or multiple vaccine doses effective for generating antibodies to both adenine and guanine.

8. The vaccine of claim 7 in which said one kind of conjugated purine contains adenine in a form selected from adenine, adenosine, and 2'-deoxyadenosine, AMP, and dAMP, and said other conjugated purine contains guanine in a form selected from guanine, guanosine, 2'-deoxyguanosine, GMP, and dGMP.

9. The method of increasing the resistance of domestic animals to pathogenic cellular microorganisms which liberate purines as a defense against polymorphonuclear neutrophils, comprising parenterally administering to the animals subject to infection by the microorganism at least one vaccine dose of a sterile aqueous solution of at least one purine conjugated to an antigenic protein, said conjugated purine containing adenine or guanine as a base, nucleoside or nucleotide thereof, the amount of said conjugated purine administered being effective to generate antibodies to adenine and/or guanine.

10. The method of claim 9 in which said animals are selected from cattle, swine, sheep, horses, and poultry.

11. The method of claim 9 or claim 10 in which at least one of said conjugated purines contains adenosine.

12. The method of claim 9 or claim 10 in which at least one of said conjugated purines contains guanosine.

13. The method of claim 9 or claim 10 in which said vaccine comprises a mixture of adenosine and guanosine conjugated to antigenic protein.

14. The method of increasing the resistance of domestic animals to pathogenic cellular microorganisms which liberate purines as a defense against polymorphonuclear neutrophils, comprising parenterally administering to animals subject to infection by the microorganism at least one vaccine dose of a sterile aqueous solution of a mixture of at least two types of purines conjugated to antigenic protein, one of said types of conjugated purines containing adenine and the other type containing guanine, said purines being present in the form of bases, nucleosides, or nucleotides, the amount of each of said kinds of conjugated purines in said vaccine dose being effective for generating antibodies to both types of said purines.

15. The method of claim 14 in which said one conjugated purine contains adenosine and said other conjugated purine contains guanosine.

16. The method of claim 9 or claim 14 in which said animals are cattle and said microorganism is *Brucella abortus*.

17. The method of claim 9 or claim 14 in which said animals are cattle and said microorganism is *Haemophilus somnus*.

* * * * *